United States Patent
Hewitt

(10) Patent No.: US 10,952,890 B2
(45) Date of Patent: Mar. 23, 2021

(54) ADHESIVE SECURING MEMBER FOR AN OSTOMY PRODUCT

(71) Applicant: Pelican Healthcare Limited, Cardiff (GB)

(72) Inventor: Aaron Hewitt, Down (GB)

(73) Assignee: PELICAN HEALTHCARE LIMITED, Cardiff (GB)

( * ) Notice: Subject to any disclaimer, the term of this patent is extended or adjusted under 35 U.S.C. 154(b) by 367 days.

(21) Appl. No.: 15/559,882

(22) PCT Filed: Mar. 21, 2016

(86) PCT No.: PCT/GB2016/050773
§ 371 (c)(1),
(2) Date: Sep. 20, 2017

(87) PCT Pub. No.: WO2016/151303
PCT Pub. Date: Sep. 29, 2016

(65) Prior Publication Data
US 2018/0055679 A1    Mar. 1, 2018

(30) Foreign Application Priority Data
Mar. 20, 2015    (GB) .................................... 1504779

(51) Int. Cl.
*A61F 5/443* (2006.01)
*A61F 5/445* (2006.01)
*A61F 5/44* (2006.01)

(52) U.S. Cl.
CPC ............ *A61F 5/443* (2013.01); *A61F 5/4404* (2013.01); *A61F 5/445* (2013.01)

(58) Field of Classification Search
CPC ........ A61F 5/443; A61F 5/4404; A61F 5/445; A61F 5/44; A61F 5/449; A61F 5/448; A61F 2007/0001–0047; A61F 13/00–00046; A61F 2/38
See application file for complete search history.

(56) References Cited

U.S. PATENT DOCUMENTS

| 3,039,464 A | 6/1962 | Esperanza |
| 4,327,727 A * | 5/1982 | Prahl ..................... A61F 5/443 604/342 |
| 8,734,412 B1 * | 5/2014 | Pacelli ................... A61F 5/445 604/337 |

(Continued)

FOREIGN PATENT DOCUMENTS

| EP | 0882437 A2 | 12/1998 |
| GB | 2397230 A | 7/2004 |

(Continued)

*Primary Examiner* — Adam Marcetich
*Assistant Examiner* — Meagan Ngo
(74) *Attorney, Agent, or Firm* — Dinsmore & Shohl LLP

(57) ABSTRACT

An adhesive flange extender for an ostomy flange comprises a flexible arcuate membrane having a radial inner edge, a radial outer edge, and an adhesive surface for securing the membrane simultaneously to the skin of an ostomate and to an ostomy flange. The membrane includes at least two independently movable tab portions at the radial outer edge of the membrane. The membrane further includes a central region and a border region that is thinner than the central region to provide increased flexibility at the periphery of the flange extender.

11 Claims, 3 Drawing Sheets

(56) References Cited

U.S. PATENT DOCUMENTS

| | | | |
|---|---|---|---|
| 9,907,689 B2* | 3/2018 | Persichina | A61F 5/4404 |
| 2003/0093042 A1* | 5/2003 | Leisner | A61F 5/448 |
| | | | 604/337 |
| 2006/0195053 A1* | 8/2006 | Oelund | A61F 5/443 |
| | | | 602/43 |
| 2007/0078418 A1* | 4/2007 | May | A61F 5/443 |
| | | | 604/336 |
| 2013/0138063 A1* | 5/2013 | Wiltshire | A61F 5/443 |
| | | | 604/344 |
| 2014/0276501 A1* | 9/2014 | Cisko | A61F 5/455 |
| | | | 604/344 |

FOREIGN PATENT DOCUMENTS

| | | | | |
|---|---|---|---|---|
| GB | 2432120 A | 5/2007 | | |
| GB | 2473667 A | 3/2011 | | |
| JP | H10248867 A | 9/1998 | | |
| JP | 2001087299 A | 4/2001 | | |
| JP | 2013505097 A | 2/2013 | | |
| WO | 2004087004 A2 | 10/2004 | | |
| WO | 200906900 A1 | 1/2009 | | |
| WO | WO-2011129738 A1 * | 10/2011 | | A61F 5/445 |

* cited by examiner

ADHESIVE SECURING MEMBER FOR AN OSTOMY PRODUCT

The present invention relates to an adhesive securing member for an ostomy flange, and in particular to an adhesive ostomy flange extender.

An ostomy pouch assembly typically consists of a collection pouch and a mounting for attaching the collection pouch to a patient, or 'ostomate's', body. The ostomy pouch mounting typically comprises an adhesive disc having a hydrocolloid skin barrier layer for contacting and adhering to the ostomate's skin. A central aperture in the mounting provides a portal opening through which the stoma extends into the collection pouch. The collection pouch is secured to the mounting disc inwardly of the outer edge of the disc, such that a flange region is defined at the outer periphery of the disc.

Adhesion of the mounting disc to the skin of the patient forms a seal that surrounds the stoma and prevents leaks. The curved, irregular nature of the shape of a patient's body means that the disc does not secure to a flat surface. Furthermore, the shape of the patient's body will shift, expand and contract with movement, causing the disc to be stretched and distorted in use. This can result in failure of the seal between the disc and the patient's skin, leading to leakage of waste from the collection pouch, causing discomfort and embarrassment to the patient.

It is therefore known to provide additional adhesive members, commonly referred to as 'flange extenders', to provide additional security where required. Flange extenders are arc shaped flexible members, typically formed of a hydrocolloid material, and including an adhesive surface for securing in part to the patient and in part to the mounting disc. The semi-circular arc shape of the flange extender is configured to sit over and overlap the outer edge of the mounting disc. The flange extender provides additional adhesion to more securely hold the mounting disc in place, as well as providing an extra sealing barrier.

However, flange extenders are subject to the same distorting forces that stretch and crease the mounting disc, and the these same forces can also cause the flange extender to crease or fold, which compromises the seal.

It is therefore desirable to provide an improved flange extender that addresses the above described problems and/or which provides improvements generally.

According to the present invention there is provided an adhesive securing member for an ostomy pouch mounting disc as described in the accompanying claims.

In an embodiment of the invention there is provided an adhesive securing member for an ostomy product comprising a flexible arcuate membrane having a radial inner edge, a radial outer edge, and an adhesive surface for securing the membrane simultaneously to the skin of an ostomate and to an ostomy flange. The membrane includes at least two independently movable tab portions at the radial outer edge of the membrane.

The independently movable tabs enable sections of the outer part of the membrane to flex independently to each other, thereby minimising shear forces that may lead to peeling of the membrane that may compromise the seal and potentially lead to a complete loss of adhesion. The increased flexibility of the outer edge also provides improved comfort by reducing pulling effects of the membrane on the skin of the ostomate.

The adhesive securing member preferably comprises a first end, a second end, and at least one slit formed in the membrane, the at least one slit extending inwards from an open first end located at the radial outer edge and a second end spaced radially outwards of the radial inner edge of the membrane, the at least one slit defining the at least two movable tabs. The slits may extend inwardly in any given direction from a part of the outer edge towards a part of the inner edge that need not be radially aligned. The term 'inwards' includes any direction in which the slit extends inboard of the outer edge.

The at least one slit preferably extends inwards in a radial direction. Alternatively, the slits extending inwardly from the outer edge may be arranged parallel to each other or at diverging or intersecting angles or any other suitable configuration.

Preferably the flexible membrane is formed at least in part from a flexible polymer material having a contact adhesive layer that is suitable for safely and securely adhering to the skin, and a backing layer. Preferably the membrane is formed from a hydrocolloid material.

The membrane preferably comprising a plurality of slits arranged at angularly spaced locations along the outer edge of the arcuate membrane. The plurality of slits increase the number of tabs and hence the flexibility of the outer portion of the membrane.

Each of the slits preferably comprises a channel having spaced side walls, an end wall, and a mouth located at the radial outer edge of membrane. The spaced form of the channel prevents interference between the tabs during flexing.

Preferably the side edges of each channel curve outwardly at the outer edge of the membrane to define an outwardly flared mouth. This radiussed mouth profile prevents the corners of each adjacent tab from interfering with each other.

Preferably the width of each channel tapers inwardly towards the second end.

Preferably the arcuate membrane spans a centre angle of substantially 180 degrees. The membrane preferably also comprises four slits defining five independently movable tabs, which has been found to be the optimum configuration for a 180 degree membrane.

Preferably the flexible membrane is a substantially planar membrane having a planar lower surface and wherein the lower surface is an adhesive surface.

Preferably the width of the membrane at its lengthwise centre is greater than its width at the first and second ends.

Preferably the radial inner edge has a constant radius and the radius of the radial outer edge increases from the first and second ends towards the centre.

Preferably the second ends of the slits are aligned along a line of constant radius. This ensures that an arcuate band of adhesive of constant thickness is located between the ends of the slits and the outer edge of the ostomy flange in use.

Preferably the second ends of the slits are equally spaced from the radial inner edge of the membrane.

Preferably the membrane has an outer border section along at least the radially outer edge and a central region located radially inwards of the border region, the border region having a reduced thickness relative to the central region. The membrane therefore has a banded configuration with a thinner outer banded region and a thicker inner banded region. Preferably the border region extends around peripheral edge of the membrane, and may extend around the entire periphery of the central section. The reduced thickness makes the border section more flexible and pliable than the central section, thereby improving conformity to the contours of the patient's body while the thicker central region maintains the strength of the membrane to prevent tearing.

The membrane preferably has a lower surface which comprises the adhesive surface, and an upper surface. The border section and central section are coplanar at the lower surface such that the lower surface is flat across its entire area. The height of the upper surface increases from the border section to the central section to define the change in thickness.

Preferably the slits are formed in the border section only. The slits are also preferably formed in the border section along at least the radially outermost edge of the membrane. The term 'slits' refers to an arrangement in which a complete break is formed which extends entirely through the membrane from its upper surface to its lower surface.

Preferably the central region includes recesses aligned with and corresponding to the slits. The recesses comprise a decreases thickness region where the thickness is less than the thickness of the central region and is preferably the same thickness as the border section. The recesses correspond in shape to the slits, having an open mouth tapering to an inner end. The outer edges of the recesses are radially spaced inwards of the inner edges of the slits with the recesses and slits being separated by a region of the border section.

The present invention will now be described by way of example only with reference to the following illustrative figure in which.

Figure 1:
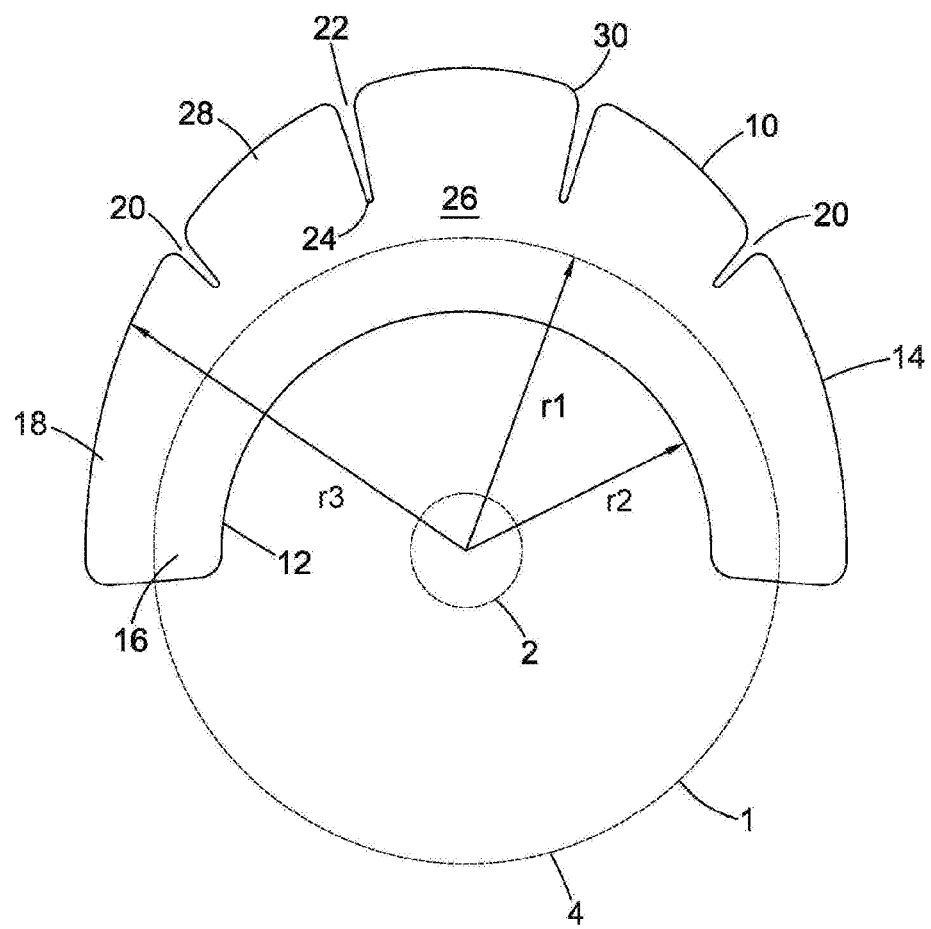
FIG. 1 is a plan view of a flange extender according to an embodiment of the present invention with an ostomy flange indicated in phantom line.

Referring to FIG. 1, an ostomy flange 1 is provided for mounting an ostomy pouch to an ostomate. The ostomy flange 1 is a mounting disc having a radius r1. The ostomy flange 1 comprises a flexible pad having an adhesive polymer material such as a hydrocolloid skin layer. The flange 1 may also include additional layers such as foam and/or polymer layers secured to the outer surface of the hydrocolloid layer. The ostomy flange 1 includes a central aperture 2 for receiving the stoma of the ostomate. The peripheral edge 4 has a diameter selected to provide the disc with an acceptable adhesive surface area.

Typically the ostomy flange 1 will be secured to a mounting plate formed from a flexible plastic material that is secured to the ostomy pouch. The mounting plate includes an aperture which aligns with the aperture 2 of the ostomy flange 1. The ostomy flange 1 secures the mounting plate and the ostomy pouch to the ostomate's skin, and provides a seal about the inlet aperture to the pouch.

A flange extender 10 is provided to extend the adhesive surface area of the ostomy flange 1 and improve securement of the ostomy flange 1 to the ostomate. The flange extender 10 has an arcuate shaped body 11 formed from a flexible hydrocolloid material. However, it will be appreciated that any other material suitable for providing a skin barrier may be used. The body 11 of the flange extender 10 has an inner edge 12 having an inner radius r2, and an outer edge 14 having an outer radius r3. The arcuate body 11 of FIG. 1 has central angle of approximately 180 degrees such that two flange extenders 10 may be abutted together end to end to secure around the entire 360 degrees of the ostomy flange 1.

The inner radius r2 is selected to be less than the radius r1 of the ostomy flange such that the inner edge 12 of the flange extender 10 inwardly overlaps the ostomy flange 1. The lower adhesive surface of the overlapping portion 16 of the flange extender 10 adheres to the upper non-adhesive surface of the ostomy flange 1 to secure and seal the flange extender 10 thereto. The extension portion 18 of the flange extender 10 extends radially outwards of the outer edge 4 of the ostomy flange 1, with the extension portion 18 being defined as the portion of the flange extender 10 between the outer edge 4 of the ostomy flange 1 and the outer edge 14 of the extender 10. The lower adhesive surface of the extension portion 18 adheres directly to the skin of the ostomate.

It is important to maintain the adhered seal between the extension portion 18 and skin surface. The seal may be broken, particularly around the outer edges, when movement of the ostomate's body causes bending and rippling of a flange extender. To maintain the integrity of the seal, the flange extender 10 is provided with a plurality of slits 20. The slits 20 extend radially inwards from an open outer end 22 at the outer edge 14 of the flange extender 10 to an inner end 24. The length of the slits 20 is selected such that their inner ends 22 are spaced radially outwards from the outer edge 4 of the flange 1. This ensures that an adhesive zone 26 is located between the ends of the slits 20 and the outer edge 4 of the flange 1 to maintain a continuous and unbroken seal around the outer edge 4. The term "slit" may include any feature that provides a separation between angularly adjacent portions of the extender, including an elongate cut, channel, or scallop.

The slits 20 of the embodiment of FIG. 1 comprise elongate, narrow channels tapering inwardly width wise from the opening at the first end 22 defining a mouth to the inner end 24. The slits 20 define a plurality of independently movable tabs or 'petals' 28 arranged around the radially outer part of the extension portion 18. The tabs 28, by virtue of their physical separation by the slits 20, may freely move relative to each other to accommodate the changing contours of an ostomate's body with the physical disconnect preventing the tab from imposing shear forces on each other as they are moved in opposing directions as would occur if the tab portions remained physically connected as part of a standard flange extender. It is these shear forces which cause the edges to pull away from the skin thereby breaking the seal and potentially leading to a complete loss of adhesion in arrangements of the prior art.

The outer corners 30 of the tabs 28 are preferably radiussed providing outwardly curved leading edges into the mouth 22. The adjacent corners 30 of adjacent tabs 28 therefore curve away from each other increasing separation and preventing the corners from catching each other during movement. In the arrangement shown in FIG. 1 there is provided 4 slits 20 defining 5 tabs 28. The tabs 28 are arranged such that the tabs 28 at either end of the flange extender 10 are longer than the other three tabs 28 to ensure a larger uninterrupted sealing surface towards the ends. It has been found that for a 180 degree semi-circular flange extender this is the optimum arrangement that balances flexibility with optimum adhesion. It will however be appreciated that other tab configurations may be provided within the scope of the invention, with less or more tabs provided as required. It will also be appreciated that the flange extender may span an angle greater than or less than 180 degrees. Where the angle is less than 180 degrees, more than 2 extenders are required to encircle the ostomy flange 1.

Figure 2:
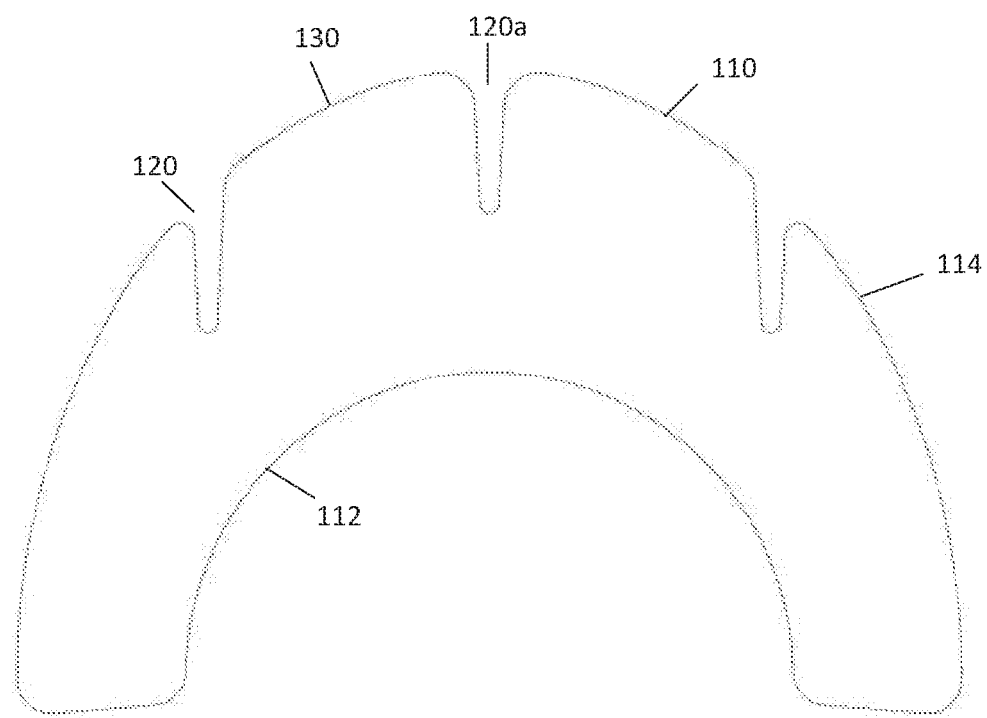
FIG. 2 is a plan view of a flange extender according to another embodiment of the present invention.

Referring to FIG. 2, in an alternative embodiment of the invention the flange extender 110 includes an inner edge 112 and outer edge 114. The slots 120 are formed in the outer edge 114 and extend inwardly towards the inner edge 112. The slots 120 define independently movable tabs 130. The slots 120 are arranged parallel to each other. The circumferentially central slot 120a extends in a radial direct towards the centre of the arc. The outer slots 120 extend in the same direction, parallel to slot 120a. This arrangement of slots 120 allows the flange extender 110 to fold and confirm to the ostomate's body in a different way to the slot arrangement of FIG. 1. Similarly, other slots configurations may be provided that are tailored to the different patient requirements.

Figure 3:
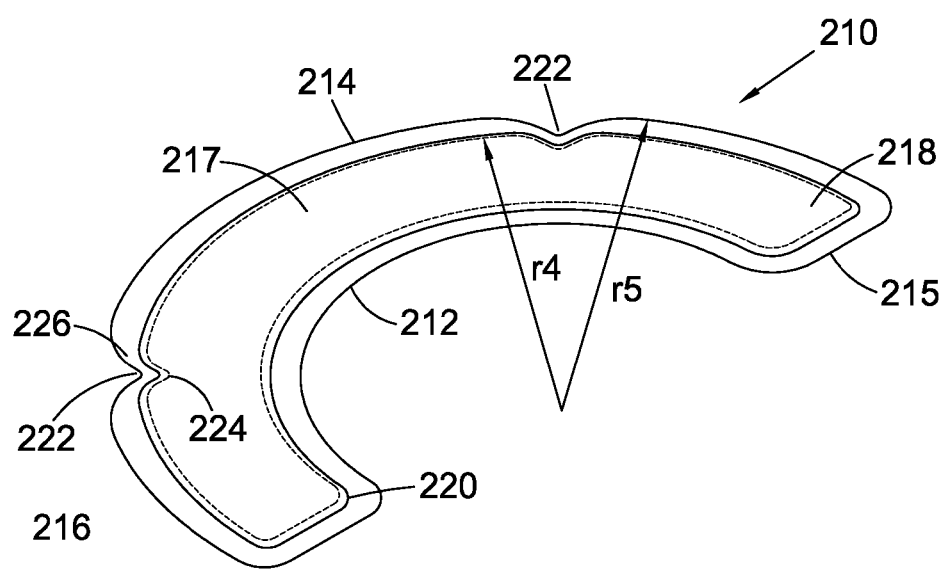
FIG. 3 is a flange extender according to another embodiment of the present invention.

In an alternative embodiment shown in FIG. 3 a flange extender 210 has an inner edge 212 and an outer edge 214. The extender 210 includes an outer peripheral band defining a border region 216 that extends around its peripheral edge. The border region 216 has a first thickness t1. The border region 216 borders a central region 218 having a second thickness t2 which is greater than the thickness t1 of the border region 216. The lower surface 215 of the flange extender 210 which in use adheres to the patient's skin, is planar, with the border region 216 and central region 218 being coplanar along that lower surface 215 ensuring a flat bonding surface. The variation in thickness occurs on the upper surface 217 with the height of the upper surface 217 increasing from the border region 216 to the central region 218. The central region 218 has a tapered outer edge 220 that slopes downwardly to the border region 216. The thinner border region 216 has a greater flexibility than the thicker central region 218. A pair of slots 222 are formed in the flexible border region 216. The slits 222 are substantially v-shaped, being wider at their opening and tapering radially inwards. In other embodiments the slits may have alternate forms. The slits 222 extend radially into the border region 216 and terminate radially outwards of the central region 218.

The central region 218 has an outer radius r4 which is less than the outer radius r5 of the flange extender 210. The central region 218 includes recesses 224 which are angularly aligned with the slits 222. The slits 222 extend radially inwards to a radial distance inwardly of the outer radius r4 of the central region. The recesses 224 also extend radially inwards and have a v-shaped form corresponding to the form of the slits 222. The recesses 224 ensure that the central region 218 remains inwardly spaced from the slits 222, with and band 226 of the thinner border region 216 separating the slits 22 from the central region 218 at this location, with the border region 216 preferably extending around the entire periphery of the central region 218. The recesses 224 maximise the flexibility in the region of the slits 222, with the greater width of the central region 218 around the remaining sections of the flange extender 210 maximising integrity.

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

The invention claimed is:

1. A flange extender for an ostomy product of a type having an ostomy flange with a central aperture adapted to receive a stoma and an outer perimeter spaced from the aperture, the flange extender comprising:
    a flexible curved membrane having a radial inner edge, a radial outer edge, a lower adhesive surface adapted to secure the membrane, when in use, simultaneously to a wearer's skin and to the ostomy flange, and an opposing upper surface which is a non-adhesive backing layer that, when in use, faces away from the wearer's skin, the upper surface of the membrane having a height;
    the membrane comprising slits extending into the membrane to form at least two independently movable tab portions at the radial outer edge of the membrane; and
    the membrane further having an outer border region and a central region located radially inwards of the outer border region with the outer border region surrounding an entire periphery of the central region and the slits extending inwards from an open first end located at the radial outer edge to a second end spaced radially outwards of the radial inner edge of the membrane and being formed only in the outer border region with the central region being inwardly spaced from the slits, the lower adhesive surface being generally planar in the outer border region and the central region, with the outer border region and the central region being coplanar to define a flat bonding surface, the height of the non-adhesive backing layer increasing from the outer border region to the central region to define a change in thickness such that the outer border region has a reduced thickness and increased flexibility relative to the central region;
    wherein the flange extender is adapted to engage the outer perimeter of the ostomy flange, spaced from the central aperture, with the reduced thickness of the outer border region adapted to engage the wearer's skin.

2. The flange extender according to claim 1, wherein the flexible curved membrane is formed from a flexible polymer material.

3. The flange extender according to claim 2, wherein the membrane is formed from a hydrocolloid material.

4. The flange extender according to claim 1, wherein the slits are arranged at angularly spaced locations along the radial outer edge of the membrane.

5. The flange extender according to claim 4, wherein each of the slits comprises a channel having spaced side walls, an end wall, and a mouth located at the radial outer edge of membrane.

6. The flange extender according to claim 5, wherein the side edges of each channel curve outwardly at the radial outer edge of the membrane to define an outwardly flared mouth.

7. The flange extender according to claim 5, wherein a width of each channel tapers inwardly towards the second end.

8. The flange extender according to claim 1, wherein the membrane has a first end and an opposing second end and a lengthwise centre located between the first and second ends, a width of the membrane at its lengthwise centre being greater than a width at the first and second ends.

9. The flange extender according to claim 1, wherein the radial inner edge of the membrane has a constant radius and the radial outer edge has a radius that increases from first and second ends towards a lengthwise centre.

10. The flange extender according to claim 1, wherein the increased thickness of the central region is adapted to maintain strength of the membrane to prevent tearing.

11. The flange extender according to claim 1, wherein the outer border region of the membrane further includes a radial inner edge, and the height of the outer border region along the radial outer edge as well as the radial inner edge is reduced in thickness relative to the central region.

* * * * *